(12) United States Patent
Gerardi et al.

(10) Patent No.: US 12,370,171 B2
(45) Date of Patent: *Jul. 29, 2025

(54) ORAL CANNABINOID PRODUCT WITH LIPID COMPONENT

(71) Applicant: Nicoventures Trading Limited, London (GB)

(72) Inventors: Anthony Richard Gerardi, Winston-Salem, NC (US); Thomas H. Poole, Winston-Salem, NC (US); Michael Andrew Zawadzki, Clemmons, NC (US); Kristen Ann Spielbauer, Kernersville, NC (US); Steven Lee Alderman, Lewisville, NC (US); Timothy Brian Nestor, Advance, NC (US)

(73) Assignee: NICOVENTURES TRADING LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/502,663

(22) Filed: Nov. 6, 2023

(65) Prior Publication Data

US 2024/0131002 A1  Apr. 25, 2024

Related U.S. Application Data

(63) Continuation of application No. 17/104,926, filed on Nov. 25, 2020, now Pat. No. 11,839,602.

(51) Int. Cl.
*A61K 31/352* (2006.01)
*A61K 9/16* (2006.01)
*A61K 31/05* (2006.01)
*A61K 47/24* (2006.01)
*A61K 47/26* (2006.01)
*A61K 47/44* (2017.01)

(52) U.S. Cl.
CPC .......... *A61K 31/352* (2013.01); *A61K 9/1694* (2013.01); *A61K 31/05* (2013.01); *A61K 47/24* (2013.01); *A61K 47/26* (2013.01); *A61K 47/44* (2013.01)

(58) Field of Classification Search
CPC ........ A61K 31/05; A61K 47/24; A61K 47/26; A61K 47/44
See application file for complete search history.

(56) References Cited

U.S. PATENT DOCUMENTS

| 2007/0148283 A1* | 6/2007 | Harvey | A23L 27/2054 426/3 |
| 2020/0022945 A1* | 1/2020 | Swartout | A61K 9/0056 |
| 2020/0037638 A1* | 2/2020 | Faraci | A61K 9/1075 |
| 2020/0138705 A1* | 5/2020 | Wan | A23G 3/42 |

* cited by examiner

*Primary Examiner* — Jianfeng Song
(74) *Attorney, Agent, or Firm* — Womble Bond Dickinson (US) LLP; Scott R. Breining

(57) ABSTRACT

Meltable compositions configured for oral use, the compositions including at least one cannabinoid or cannabimimetic, are provided. The compositions include one or more fillers, typically a sugar alcohol, and a lipid. A method of forming such compositions is also provided.

16 Claims, No Drawings

ORAL CANNABINOID PRODUCT WITH LIPID COMPONENT

FIELD OF THE DISCLOSURE

The present disclosure relates to compositions intended for human use. The compositions are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

BRIEF SUMMARY

The present disclosure generally provides meltable compositions configured for oral use, the compositions comprising at least one cannabinoid or cannabimimetic, at least one filler, such as a sugar alcohol, and a lipid.

In one aspect, the disclosure provides a composition in meltable form, configured for oral use, the composition including a cannabinoid or cannabimimetic, a filler; and a lipid, wherein the meltable form comprises the composition as a homogenous mixture. In some embodiments, the cannabinoid may be selected from the group consisting of cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), tetrahydrocannabivarinic acid (THCV A), and combinations thereof. In certain embodiments, the cannabinoid may be selected from the group consisting of tetrahydrocannabinol (THC), cannabidiol (CBD), and combinations thereof.

In some embodiments, the cannabinoid or cannabimimetic may be present in an amount of from about 0.1 to about 20% by weight, based on the total weight of the meltable composition. Some embodiments of meltable compositions may include one or more additional active ingredients, for example, including, but not limited to, botanical ingredients, stimulants, amino acids, nicotine components, pharmaceutical ingredients, nutraceutical ingredients, medicinal ingredients, terpenes, and combinations thereof. In certain embodiments, for example, the meltable composition may include a terpene selected from the group consisting of beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, germacrene, and combinations thereof.

In some aspects of meltable compositions according to the disclosure, the filler component may comprise at least one sugar alcohol present in an amount of from about 38 to about 58% by weight, based on the total weight of the composition, and the lipid may be present in an amount of from about 35 to about 58% by weight, based on the total weight of the composition. In some embodiments, all or a portion of the lipid has a melting point of about 29° C. or above. In certain embodiments, all or a portion of the lipid has a melting point of from about 36° C. to about 45° C. Generally, the lipid component may be an oil selected from the group consisting of palm oil, palm kernel oil, soybean oil, sunflower oil, cottonseed oil, coconut oil, and combinations thereof, wherein the oil may be hydrogenated, partially hydrogenated, or non-hydrogenated. In embodiments where the filler comprises a sugar alcohol, the sugar alcohol may be selected from the group consisting of isomalt, erythritol, sorbitol, arabitol, ribitol, maltitol, dulcitol, iditol, mannitol, xylitol, lactitol, and combinations thereof. In certain embodiments, the sugar alcohol is isomalt.

In further embodiments, meltable compositions according to the disclosure may further comprise lecithin. In such embodiments, the lecithin may be present in an amount of from about 0.5 to about 1.5% by weight, based on the total weight of the composition. In some embodiments, the lipid may be selected from the group consisting of palm oil, palm kernel oil, sunflower oil, and combinations thereof. In certain embodiments, for example, the lipid component may include palm oil, palm kernel oil, or a mixture thereof that is present in a total amount of from about 35 to about 53% by weight, and sunflower oil present in an amount of from about 2 to about 6% by weight, based on the total weight of the composition.

Some aspects of the meltable compositions according to the disclosure may include at least one additional component selected from additional active ingredients, sweeteners, salts, flavorants, buffers, emulsifiers, colorants, processing aids, and combinations thereof. In some embodiments of meltable compositions, the composition is substantially free of nicotine. In some embodiments, the composition is substantially free of tobacco.

Another aspect of the present disclosure provides a composition in meltable form, configured for oral use, the composition comprising a cannabinoid or cannabimimetic present in an amount of from about 0.1 to about 5% by weight, based on the total weight of the composition, a sugar alcohol present in an amount of from about 38 to about 58% by weight, based on the total weight of the composition, a lipid present in an amount of from about 35 to about 58% by weight, based on the total weight of the composition, a salt present in an amount of from about 0.5 to about 1.5% by weight, based on the total weight of the composition, a sweetener present in an amount of from about 0.05 to about 0.5% by weight, based on the total weight of the composition, and a flavorant present in an amount of from about 0.5 to about 1.5% by weight, based on the total weight of the composition.

Still other aspects of the present disclosure provide methods of forming a composition in meltable form and configured for oral use. In some embodiments, such methods may comprise, for example, melting a lipid to form a melted material, adding a portion of the melted material to a filler material to form a mixture, milling the mixture to form a powder, mixing the remainder of the melted material with the powder to form a base material, and mixing the base material with at least one cannabinoid or cannabimimetic to form the composition. Some embodiments of methods may further include depositing the composition into molds to form a plurality of discrete product units. In some embodiments, methods as described herein may comprise forming a premix of the at least one cannabinoid or cannabimimetic with a lipid oil prior to the mixing step, the lipid oil being liquid at room temperature. In some embodiments, the lipid oil is sunflower oil. Some embodiments of methods may further comprise mixing the base material with at least one additional component selected from additional active ingredients, sweeteners, salts, flavorants, buffers, emulsifiers, colorants, processing aids, and combinations thereof. In some embodiments, the milling step comprises milling the mixture to a particle size of about 20 microns or less.

The present disclosure includes, without limitation, the following embodiments:

Embodiment 1: A composition in meltable form, configured for oral use, the composition comprising: a cannabinoid or cannabimimetic; a filler; and a lipid, wherein the meltable form comprises the composition as a homogenous mixture.

Embodiment 2: The composition of embodiment 1, wherein the cannabinoid is selected from the group consisting of tetrahydrocannabinol (THC), cannabidiol (CBD), and combinations thereof.

Embodiment 3: The composition of any one of embodiments 1-2, wherein the cannabinoid is selected from the group consisting of cannabigerol (CBG), cannabichromene (CBC), cannabidiol (CBD), tetrahydrocannabinol (THC), cannabinol (CBN), cannabidiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), tetrahydrocannabivarinic acid (THCV A), and combinations thereof Embodiment 4: The composition of any one of embodiments 1-3, wherein the cannabinoid or cannabimimetic is present in an amount of from about 0.1 to about 20% by weight, based on the total weight of the composition.

Embodiment 5: The composition of any one of embodiments 1-4, wherein the composition further comprises an additional active ingredient selected from the group consisting of botanical ingredients, stimulants, amino acids, nicotine components, pharmaceutical ingredients, nutraceutical ingredients, medicinal ingredients, terpenes, and combinations thereof.

Embodiment 6: The composition of any one of embodiments 1-5, wherein the composition comprises a terpene selected from the group consisting of beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, germacrene, and combinations thereof.

Embodiment 7: The composition of any one of embodiments 1-6, wherein: the filler comprises at least one sugar alcohol present in an amount of from about 38 to about 58% by weight, based on the total weight of the composition; and the lipid is present in an amount of from about 35 to about 58% by weight, based on the total weight of the composition.

Embodiment 8: The composition of any one of embodiments 1-7, wherein all or a portion of the lipid has a melting point of about 29° C. or above.

Embodiment 9: The composition of any one of embodiments 1-8, wherein all or a portion of the lipid has a melting point of from about 36° C. to about 45° C.

Embodiment 10: The composition of any one of embodiments 1-9, wherein the lipid is an oil selected from the group consisting of palm oil, palm kernel oil, soybean oil, sunflower oil, cottonseed oil, coconut oil, and combinations thereof, wherein the oil may be hydrogenated, partially hydrogenated, or non-hydrogenated.

Embodiment 11: The composition of any one of embodiments 1-10, wherein the sugar alcohol is selected from the group consisting of isomalt, erythritol, sorbitol, arabitol, ribitol, maltitol, dulcitol, iditol, mannitol, xylitol, lactitol, and combinations thereof.

Embodiment 12: The composition of any one of embodiments 1-11, wherein the sugar alcohol is isomalt.

Embodiment 13: The composition of any one of embodiments 1-12, further comprising lecithin.

Embodiment 14: The composition of any one of embodiments 1-13, wherein the lecithin is present in an amount of from about 0.5 to about 1.5% by weight, based on the total weight of the composition.

Embodiment 15: The composition of any one of embodiments 1-14, wherein the lipid is selected from the group consisting of palm oil, palm kernel oil, sunflower oil, and combinations thereof.

Embodiment 16: The composition of any one of embodiments 1-15, wherein the lipid comprises: palm oil, palm kernel oil, or a mixture thereof that is present in a total amount of from about 35 to about 53% by weight; and sunflower oil present in an amount of from about 2 to about 6% by weight, based on the total weight of the composition.

Embodiment 17: The composition of any one of embodiments 1-16, further comprising at least one additional component selected from additional active ingredients, sweeteners, salts, flavorants, buffers, emulsifiers, colorants, processing aids, and combinations thereof.

Embodiment 18: The composition of any one of embodiments 1-17, wherein the composition is substantially free of nicotine.

Embodiment 19: The composition of any one of embodiments 1-18, wherein the composition is substantially free of tobacco.

Embodiment 20: A composition in meltable form, configured for oral use, the composition comprising: a cannabinoid or cannabimimetic present in an amount of from about 0.1 to about 5% by weight, based on the total weight of the composition; a sugar alcohol present in an amount of from about 38 to about 58% by weight, based on the total weight of the composition; a lipid present in an amount of from about 35 to about 58% by weight, based on the total weight of the composition; a salt present in an amount of from about 0.5 to about 1.5% by weight, based on the total weight of the composition; a sweetener present in an amount of from about 0.05 to about 0.5% by weight, based on the total weight of the composition; and a flavorant present in an amount of from about 0.5 to about 1.5% by weight, based on the total weight of the composition.

Embodiment 21: A method for forming a composition in meltable form and configured for oral use, comprising: (a) melting a lipid to form a melted material; (b) adding a portion of the melted material to a filler material to form a mixture; (c) milling the mixture to form a powder; (d) mixing the remainder of the melted material with the powder to form a base material; (e) mixing the base material with at least one cannabinoid or cannabimimetic to form the composition.

Embodiment 22: The method of embodiment 21, further comprising depositing the composition into molds to form a plurality of discrete product units.

Embodiment 23: The method of any one of embodiments 21-22, further comprising forming a premix of the at least one cannabinoid or cannabimimetic with a lipid oil prior to mixing step (e), the lipid oil being liquid at room temperature.

Embodiment 24: The method of any one of embodiments 21-23, wherein the lipid oil is sunflower oil.

Embodiment 25: The method of any one of embodiments 21-24, further comprising mixing the base material with at least one additional component selected from additional active ingredients, sweeteners, salts, flavorants, buffers, emulsifiers, colorants, processing aids, and combinations thereof.

Embodiment 26: The method of any one of embodiments 21-25, wherein the milling step comprises milling the mixture to a particle size of about 20 microns or less.

These and other features, aspects, and advantages of the disclosure will be apparent from a reading of the following detailed description. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

The present disclosure provides compositions configured for oral use, the compositions comprising one or more active ingredients, a lipid, and one or more fillers. The one or more fillers generally comprise a sugar alcohol or a combination of sugar alcohols. The active ingredient typically includes a cannabinoid or cannabimimetic, e.g., such as tetrahydrocannabinol (THC), cannabidiol (CBD), or a combination thereof. The compositions are in the form of a melt. In some embodiments, the compositions may further comprise additional active ingredients, binders, organic acids, water, sweeteners, salts, flavors, buffers, emulsifiers, colorants, processing aids, and combinations thereof. The relative amounts of the various components within the composition may vary, and typically are selected so as to provide the desired sensory and performance characteristics to the oral composition. The example individual components of the composition are described herein below.

Filler

The compositions as described herein comprise one or more fillers. Fillers may fulfill multiple functions, such as enhancing certain organoleptic properties such as texture and mouthfeel, enhancing cohesiveness or compressibility of the product, and the like.

The amount of filler can vary, but is typically greater than about 20%, and up to about 75% of the composition by weight, based on the total weight of the composition. A typical range of filler within the composition can be from about 20 to about 75% by total weight of the composition, for example, from about 20, about 25, or about 30, to about 35, about 40, about 45, or about 50% by weight (e.g., about 20 to about 50%, or about 25 to about 45% by weight). In certain embodiments, the amount of filler is at least about 20% by weight, such as at least about 25%, or at least about 30%, or at least about 35%, or at least about 40%, based on the total weight of the composition. In some embodiments, the amount of filler within the composition can be from about 38 to about 58% by total weight of the composition.

Generally, fillers are porous particulate materials and are cellulose-based. For example, suitable fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential fillers include maltodextrin, dextrose, calcium carbonate, calcium phosphate, lactose, mannitol, xylitol, and sorbitol. Combinations of fillers can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the composition based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "genetically modified" starches. Other starches are obtained and subsequently modified by chemical, enzymatic, or physical means. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, acetylation, hydroxypropylation, and/or partial hydrolysis. Enzymatic treatment includes subjecting native starches to enzyme isolates or concentrates, microbial enzymes, and/or enzymes native to plant materials, e.g., amylase present in corn kernels to modify corn starch. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, and starch sodium octenyl succinate.

Additional examples of potential fillers include maltodextrin, dextrose, calcium carbonate, calcium phosphate, lactose, and sugar alcohols. Combinations of fillers can also be used. In some embodiments, the filler comprises or is a mixture of glucose and starch-derived polysaccharides. One such suitable mixture of glucose and starch-derived polysaccharides is EMDEX®, available from JRS PHARMA LP, USA, 2981 Route 22, Patterson, NY 12563-2359.

In some embodiments, the filler comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). Isomalt is an equimolar mixture of two disaccharides, each composed of two sugars as follows: glucose and mannitol ($\alpha$-D-glucopyranosido-1,6-mannitol); and glucose and sorbitol ($\alpha$-D-glucopyranosido-1,6-sorbitol). In some embodiments, the one or more sugar alcohols comprise isomalt. In some embodiments, the one or more sugar alcohols is isomalt.

In some embodiments, the filler comprises a combination of isomalt and EMDEX®. In some embodiments, the one or more sugar alcohols is a combination of isomalt and EMDEX®.

In some embodiments, the one or more sugar alcohols is a combination of two or even three sugar alcohols. In some embodiments, the combination of sugar alcohols comprises or is isomalt and maltitol.

The total amount of sugar alcohols can vary, but is typically greater than about 30%, and up to about 95% of the composition by weight, based on the total weight of the composition. A typical range of sugar alcohols within the composition can be for example, from about 35, about 40, about 45, about 50, or about 55, to about 60, about 65, about 70, about 75, about 80, about 85, about 90, or about 95%, by weight. In certain embodiments, the amount of sugar alcohol is at least about 50% by weight, such as is at least about 55% by weight, or at least about 60%, or at least about 65%, or at least about 70%, or at least about 75%, or at least about 80%, or at least about 85%, based on the total weight of the composition.

In particular embodiments, the sugar alcohol is isomalt in an amount of from about 35 to about 55% by weight, based on the total weight of the composition, such as from about 35, about 40, or about 45, to about 50 or about 55% by weight.

In particular embodiments, the sugar alcohol is a combination of isomalt in an amount of from about 10 to about 25% by weight, such as about 10, about 15, about 20, or about 25% by weight; and maltitol in an amount of from about 50 to about 75% by weight, such as about 50, about 55, about 60, about 65%, about 70, about 75% by weight.

In particular embodiments, the filler is a combination of isomalt in an amount of from about 30 to about 50% by weight, based on the total weight of the composition, such as about 30, about 35, about 40, about 45, or about 50% by weight; and a glucose-polysaccharide blend (e.g., EMDEX®) in an amount of from about 35 to about 55% by weight, based on the total weight of the composition, such as about 35, about 40, about 45, or about 50% by weight.

Lipid

In some embodiments, the composition comprises a lipid. Such compositions may, in some embodiments, be described as "meltable" or "melting" compositions, described further herein below. When present, the lipid of the composition is typically a fat, oil, or wax substance derived from animal or plant material (e.g., plant-derived fats), and typically comprises mostly triglycerides along with lesser amounts of free fatty acids and mono- or diglycerides. In certain embodiments, the lipid is a solid or semi-solid at room temperature (i.e., 25° C.) and capable of at least partially liquefying when subjected to the temperature of the oral cavity of the user (i.e., "melting"). Example plant-derived fats are comprised primarily of saturated or unsaturated fatty acid chains (most of which are bound within triglyceride structures) having a carbon length of about 10 to about 26 carbon atoms, or about 14 to about 20 carbon atoms, or about 14 to about 18 carbon atoms.

In some embodiments, the lipid comprises an oil and, in particular, a food grade oil including fractionated oils. In some embodiments, the lipid comprises a combination of oils. Such oils include, but are not limited to, vegetable oils (e.g., acai oil, almond oil, amaranth oil, apricot oil, apple seed oil, argan oil, avocado oil, babassu oil, beech nut oil, ben oil, bitter gourd oil, black seed oil, blackcurrant seed oil, borage seed oil, borneo tallow nut oil, bottle gourd oil, brazil nut oil, buffalo gourd oil, butternut squash seed oil, cape chestnut oil, canola oil, carob cashew oil, cocoa butter, cocklebur oil, coconut oil, corn oil, cothune oil, coriander seed oil, cottonseed oil, date seed oil, dika oil, egus seed oil, evening primrose oil, false flax oil, flaxseed oil, grape seed oil, grapefruit seed oil, hazelnut oil, hemp oil, kapok seed oil, kenaf seed oil, lallemantia oil, lemon oil, linseed oil, macadamia oil, mafura oil, manila oil, meadowfoam seed oil, mongongo nut oil, mustard oil, niger seed oil, nutmeg butter, okra seed oil, olive oil, orange oil, palm oil, papaya seed oil, peanut oil, pecan oil, perilla seed oil, persimmon seed oil, pequi oil, pili nut oil, pine nut oil, pistachio oil, pomegranate seed oil, poppyseed oil, pracaxi oil, prune kernel oil, pumpkin seed oil, quinoa oil, ramtil oil, rapeseed oil, rice bran oil, royle oil, sacha inchi oil, safflower oil, sapote oil, seje oil, sesame oil, shea butter, soybean oil, sunflower oil, taramira oil, tea seed oil, thistle oil, tigernut oil, tobacco seed oil, tomato seed oil, walnut oil, watermelon seed oil, wheat germ oil, and combinations thereof), animal oils (e.g., cattle fat, buffalo fat, sheep fat, goat fat, pig fat, lard, camel fat, tallow, liquid margarine, fish oil, fish liver oil, whale oil, seal oil, and combinations thereof), and mineral oils.

In certain embodiments, the plant-derived fats of the present disclosure include palm oil (including fractionated palm oil), palm kernel oil, soybean oil, cottonseed oil, and mixtures thereof. In one embodiment, the lipid is a blend of palm oil and palm kernel oil. The lipid can be, for example, hydrogenated, partially hydrogenated, or non-hydrogenated. Example embodiments of lipids can be purchased under the brand names CEBES®, CISAO®, or CONFAO®, available from AarhusKarlshamn USA Inc. or parent company, AAK AB.

The melting point of all or a portion of the lipid utilized in the composition is typically about 29° C. or above, such as about 29° C. to about 49° C., or about 36° C. to about 45° C., or about 38° C. to about 41° C. In some embodiments, use of lipids with a melting point of less than about 36° C. is not advantageous due to possible melting during product storage or handling. One test for determining the melting point of lipids is the Mettler dropping point method (ASTM D3954-15, Standard Test Method for Dropping Point of Waxes, ASTM International, West Conshohocken, P A, 2015, www.astm.org.).

When present, the amount of lipid within the composition may vary. In certain embodiments, the amount of lipid is at least about 10 percent, at least about 20 percent, or at least about 30 percent, on a dry weight basis of the composition. In certain embodiments, the amount of lipid is less than about 70 percent, less than about 60 percent, or less than about 50 weight percent, on a dry weight basis. Example lipid weight ranges include about 10 to about 70 dry weight percent, such as about 35 to about 50 dry weight percent. In some embodiments, the amount of lipid is about 35, about 40, about 45, or about 50 percent by weight of the total composition. In some embodiments, the amount of lipid within the composition can be from about 35 to about 58% by total weight of the composition.

In some embodiments, the composition comprises a lipid. In one embodiment, the lipid is an oil selected from the group consisting of palm oil, palm kernel oil, soybean oil, sunflower oil, cottonseed oil, coconut oil, and combinations thereof, wherein the oil may be hydrogenated, partially hydrogenated, or non-hydrogenated. In one embodiment, the lipid is a fractionated non-hydrogenated cocoa butter substitute such as CEBES® 29-04 NH, available from AarhusKarlishartin USA, 131 Marsh Street, Port. Newark, NJ 07114.

Cannabinoid

In some embodiments, the active ingredient comprises at least one cannabinoid. As used herein, the term "cannabinoid" refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in *cannabis*; and synthetic cannabinoids, manufactured artificially.

*Cannabis* species express at least 85 different phytocannabinoids, and are divided into subclasses, including cannabigerols, cannabichromenes, cannabidiols, tetrahydrocannabinols, cannabinols and cannabinodiols, and other cannabinoids. Cannabinoids found in *cannabis* include, without limitation: cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), tetrahydrocannabivarinic acid (THCV A), and combinations thereof. In certain embodiments, the cannabinoid is selected from tetrahydrocannabinol (THC), the primary psychoactive compound in *cannabis*, and cannabidiol (CBD) another major constituent of the plant, but which is devoid of psychoactivity. All of the above compounds can be used in the form of an isolate from plant material or synthetically derived.

Alternatively, or in addition, the active ingredient can be a cannabimimetic, which is a class of compounds derived from plants other than *cannabis* that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids, which can be used singly or in combination.

The particular percentages of cannabinoid or cannabimimetic present will vary depending upon the desired characteristics of the particular product. Typically, a cannabinoid (e.g., CBD), cannabimimetic, or combinations thereof are present in a total concentration of at least about 0.1% by weight of the composition, such as in a range from about 0.1% to about 30%, such as, e.g., from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the composition.

In certain embodiments, the cannabinoid or cannabimimetic can be premixed with a lipid oil to form a premixed solution that can be conveniently incorporated into a manufacturing process for the meltable product. In some embodiments, the cannabinoid or cannabimimetic may be in the form of a solid at room temperature and the addition/ premixing of the cannabinoid or cannabimimetic with a lipid oil (e.g., such as sunflower oil) can dissolve the cannabinoid or cannabimimetic and allow for uniform distribution of the cannabinoid or cannabimimetic within the premix solution. Use of a lipid oil as a premix partner for the cannabinoid or cannabimimetic may also provide good compatibility of the premixed solution with the remaining lipid components of the meltable product. In some embodiments, the cannabinoid or cannabimimetic can be dissolved in a heated portion of the of lipid oil having a higher melting point prior to being incorporated with the remaining lipid components of the meltable product.

Typically, the lipid oil is liquid at room temperature, with non-limiting examples including any of the vegetable oils noted herein, particularly sunflower oil. In addition to being a liquid at room temperature, the lipid oil may also enhance absorption of the cannabinoid or cannabimimetic within the oral cavity. In certain embodiments, the cannabinoid or cannabimimetic can be premixed with sunflower oil, in particular. Generally, sunflower oil is a liquid at room temperature and may act to improve the melting properties of the overall meltable product and components thereof (e.g., such as other lipid components, cannabinoids, other actives, filler material, polyols, and the like). For example, use of sunflower oil in the premix solution can affect the melting point of the resulting meltable product and provide more desirable texture theein. The premix typically contains a weight ratio of cannabinoid or cannabimimetic to lipid oil of between about 1:1 to about 1:4. In one embodiment, the lipid oil is present in an amount of about 2 to about 6% by weight, based on the total weight of the composition.

Additional Active Ingredient

The compositions disclosed herein can further include an additional active ingredient (i.e., in addition to the cannabinoid or cannabimimetic). As used herein, an "active ingredient" refers to one or more substances belonging to any of the following categories: API (active pharmaceutical ingredient), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods." These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, nicotine components, and/or pharmaceutical, nutraceutical, and medicinal ingredients (e.g., vitamins, such as A, B3, B6, B12, and C). Each of these categories is further described herein below. The particular choice of active ingredients will vary depending upon the desired flavor, texture, and desired characteristics of the particular product.

In certain embodiments, the active ingredient is selected from the group consisting of caffeine, taurine, GABA, theanine, vitamin C, lemon balm extract, ginseng, citicoline, sunflower lecithin, and combinations thereof. For example, the active ingredient can include a combination of caffeine, theanine, and optionally ginseng. In another embodiment, the active ingredient includes a combination of theanine, gamma-amino butyric acid (GABA), and lemon balm extract. In a further embodiment, the active ingredient includes theanine, theanine and tryptophan, or theanine and one or more B vitamins (e.g., vitamin B6 or B12). In a still further embodiment, the active ingredient includes a combination of caffeine, taurine, and vitamin C.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Terpenes

Active ingredients suitable for use in the present disclosure can also be classified as terpenes, many of which are associated with biological effects, such as calming effects. Terpenes are understood to have the general formula of $(C_5H_8)$, and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). In some embodiments, the compositions as disclosed herein can be characterized as free of any tobacco material (e.g., any embodiment as disclosed herein may be completely or substantially free of any tobacco material). By "substantially free" is meant that no tobacco material has been intentionally added. For example, certain embodiments can be characterized as having less than 0.001% by weight of tobacco, or less than 0.0001%, or even 0% by weight of tobacco.

When present, a botanical is typically at a concentration of from about 0.01% w/w to about 10% by weight, such as, e.g., from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include ashwagandha, Bacopa monniera, baobab, basil, *Centella asiatica*, Chai-hu, chamomile, cherry blossom, chlorophyll, cinnamon, citrus, cloves, cocoa, cordyceps, curcumin, damiana, *Dorstenia arifolia, Dorstenia odorata*, essential oils, eucalyptus, fennel, *Galphimia glauca*, ginger, *Ginkgo biloba*, ginseng (e.g., *Panax ginseng*), green tea, *Griffonia simplicifolia*, guarana, *cannabis*, hemp, hops, jasmine, *Kaempferia parviflora* (Thai ginseng), kava, lavender, lemon balm, lemongrass, licorice, lutein, maca, matcha, *Nardostachys chinensis*, oil-based extract of *Viola odorata*, peppermint, quercetin, resveratrol, *Rhizoma gastrodiae, Rhodiola*, rooibos, rose essential oil, rosemary, *Sceletium tortuosum*, Schisandra, Skullcap, spearmint extract, Spikenard, terpenes, tisanes, turmeric, *Turnera aphrodisiaca*, valerian, white mulberry, and Yerba mate.

In some embodiments, the active ingredient comprises lemon balm. Lemon balm (*Melissa officinalis*) is a mildly lemon-scented herb from the same family as mint (Lamiaceae). The herb is native to Europe, North Africa, and West Asia. The tea of lemon balm, as well as the essential oil and the extract, are used in traditional and alternative medicine. In some embodiments, the active ingredient comprises lemon balm extract. In some embodiments, the lemon balm extract is present in an amount of from about 1 to about 4% by weight, based on the total weight of the composition.

In some embodiments, the active ingredient comprises ginseng. Ginseng is the root of plants of the genus Panay, which are characterized by the presence of unique steroid saponin phytochemicals (ginsenosides) and gintonin. Ginseng finds use as a dietary supplement in energy drinks or herbal teas, and in traditional medicine. Cultivated species include Korean ginseng (*P. ginseng*), South China ginseng (*P. notoginseng*), and American ginseng (*P. quinquefolius*). American ginseng and Korean ginseng vary in the type and quantity of various ginsenosides present. In some embodiments, the ginseng is American ginseng or Korean ginseng. In specific embodiments, the active ingredient comprises Korean ginseng. In some embodiments, ginseng is present in an amount of from about 0.4 to about 0.6% by weight, based on the total weight of the composition.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition. In some embodiments, the composition comprises caffeine in an amount of from about 1.5 to about 6% by weight, based on the total weight of the composition;

Amino Acids

In some embodiments, the active ingredient comprises an amino acid. As used herein, the term "amino acid" refers to an organic compound that contains amine ($—NH_2$) and carboxyl (—COOH) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine. In some embodiments, the active ingredient comprises theanine. In some embodiments, the active ingredient comprises GABA. In some embodiments, the active ingredient comprises a combination of theanine and GABA. In some embodiments, the active ingredient is a combination of theanine, GABA, and lemon balm. In some embodiments, the active ingredient is a combination of caffeine, theanine, and *ginseng*. In some embodiments, the active ingredient comprises taurine. In some embodiments, the active ingredient is a combination of caffeine and taurine.

When present, an amino acid or combination of amino acids (e.g., theanine, GABA, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

Vitamins/Minerals

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C. In some embodiments, the active ingredient is a combination of vitamin C, caffeine, and taurine.

When present, a vitamin or combination of vitamins (e.g., vitamin B6, vitamin B12, vitamin E, vitamin C, or a combination thereof) is typically at a concentration of from about 0.01% w/w to about 6% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, about 1%, about 2%, about 3%, about 4%, about 5%, or about 6% by weight, based on the total weight of the composition.

In some embodiments, the active ingredient comprises a mineral or combination of minerals. As used herein, the term "mineral" refers to a chemical compound with a defined chemical composition and a specific crystal structure that occurs naturally in pure form. In some embodiments, the active ingredient comprises a magnesium-based mineral compounds, e.g., such as magnesium gluconate, magnesium citrate, and the like. When present, a mineral or combination of minerals (e.g., magnesium gluconate, magnesium citrate, or a combination thereof) is typically at a concentration of from about 0.01% w/w to about 6% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, about 1%, about 2%, about 3%, about 4%, about 5%, or about 6% by weight, based on the total weight of the composition.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, withania somnifera, Lion's mane, and *Silybum marianum*. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Nicotine Component

In certain embodiments, the active ingredient comprises a nicotine component. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, Beitrage Tabakforschung Int., 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the composition, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the composition.

In some embodiments, the products or compositions of the disclosure can be characterized as free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

In some embodiments, the active ingredient comprises a nicotine component (e.g., any product or composition of the disclosure, in addition to comprising any active ingredient or combination of active ingredients as disclosed herein, may further comprise a nicotine component).

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl)propanoic acid), phosphatidylserine, myoinositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine. In some embodiments, the active ingredient comprises citicoline. In some embodiments, the active ingredient is a combination of citicoline, caffeine, theanine, and ginseng. In some embodiments, the active ingredient comprises sunflower lecithin. In some embodiments, the active ingredient is a combination of sunflower lecithin, caffeine, theanine, and ginseng.

The amount of API may vary. For example, when present, an API is typically at a concentration of from about 0.001% w/w to about 10% by weight, such as, e.g., from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the composition.

In some embodiments, the composition is substantially free of any API. By "substantially free of any API" means that the composition does not contain, and specifically excludes, the presence of any API as defined herein, such as any Food and Drug Administration (FDA) approved therapeutic agent intended to treat any medical condition.

Water

The moisture content (e.g., water content) of the composition, prior to use by a consumer of the product, may vary according to the desired properties. Typically, the composition, prior to insertion into the mouth of the user, is less than about 10% by weight of water, and generally is from about 0.01 to about 10% by weight of water, for example, from about 0.1 to about 1.0% by weight. In some embodiments, there may be no water intentionally added to the meltable composition other than the amount present in various components of the meltable composition.

Salts

In some embodiments, the composition comprises a salt (e.g., an alkali metal salt), typically employed in an amount sufficient to provide desired sensory attributes to the composition. Non-limiting examples of suitable salts include sodium chloride, potassium chloride, ammonium chloride, flour salt, sodium acetate, sodium citrate, calcium citrate, and the like. In some embodiments, the salt is sodium chloride, ammonium chloride, or a combination thereof. In some embodiments, the salt is trisodium citrate, calcium citrate, or a combination thereof.

When present, a representative amount of salt is about 0.1% by weight or more, about 0.5% by weight or more, about 1.0% by weight or more, or about 1.5% by weight or more, but will typically make up about 10% or less of the total weight of the composition, or about 7.5% or less, or about 5% or less (e.g., from about 0.1 to about 5% by weight or from about 0.5 to about 1.5%).

Sweeteners

In order to improve the sensory properties of the composition according to the disclosure, one or more sweeteners may be added. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, isomaltulose, stevia, honey, and the like. Examples of artificial sweeteners include sucralose, maltodextrin, saccharin, aspartame, acesulfame K, neotame, and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the sweetener is sucralose, acesulfame K, or a combination thereof.

When present, a sweetener or combination of sweeteners may make up from about 0.01 to about 20% or more of the of the composition by weight, for example, from about 0.01 to about 0.1, from about 0.1 to about 1%, from about 1 to about 5%, from about 5 to about 10%, or from about 10 to about 20% by weight, based on the total weight of the composition. In some embodiments, a combination of sweeteners is present at a concentration of from about 0.01% to about 0.1% by weight of the composition, such as about 0.01, about 0.02, about 0.03, about 0.04, about 0.05, about 0.06, about 0.07, about 0.08, about 0.09, or about 0.1% by weight of the composition. In some embodiments, a combination of sweeteners is present at a concentration of from about 0.05% to about 0.5% by weight of the composition, such as about 0.1, about 0.2, about 0.3, about 0.4, or about 0.5% by weight of the composition. In some embodiments, a combination of sweeteners is present at a concentration of from about 1% to about 3% by weight of the composition.

Flavoring Agents

In some embodiments, the composition comprises a flavoring agent. As used herein, a "flavoring agent," "flavor" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, eucalyptus, lavender, cardamom, nutmeg, cinnamon, clove, cascarilla, sandalwood, honey, jasmine, ginger, anise, sage, licorice, lemon, orange, apple, peach, lime, cherry, strawberry, trigeminal sensates, terpenes, and any combinations thereof. See also, Leffingwell et al., Tobacco Flavoring for Smoking Products, R. J. Reynolds Tobacco Company (1972), which is incorporated herein by reference. Flavoring agents also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The amount of flavoring agent utilized in the composition can vary, but is typically up to about 10% by weight, and certain embodiments are characterized by a flavoring agent content of at least about 0.1% by weight, such as about 0.5 to about 10%, about 1 to about 5%, or about 2 to about 4% weight, based on the total weight of the composition.

Taste Modifiers

In order to improve the organoleptic properties of a composition as disclosed herein, the composition may include one or more taste modifying agents ("taste modifiers") which may serve to mask, alter, block, or improve e.g., the flavor of a composition as described herein. Non-limiting examples of such taste modifiers include analgesic or anesthetic herbs, spices, and flavors which produce a perceived cooling (e.g., menthol, *eucalyptus*, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the composition may comprise a cannabinoid or other component having a bitter taste, and a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., a cannabinoid). Suitable taste modifiers include, but are not limited to, capsaicin, gamma-amino butyric acid (GABA), adenosine monophosphate (AMP), lactisole, or a combination thereof.

When present, a representative amount of taste modifier is about 0.01% by weight or more, about 0.1% by weight or more, or about 1.0% by weight or more, but will typically make up less than about 10% by weight of the total weight of the composition, (e.g., from about 0.01%, about 0.05%, about 0.1%, or about 0.5%, to about 1%, about 5%, or about 10% by weight of the total weight of the composition).

Binders

A binder (or combination of binders) may be employed in certain embodiments, in amounts sufficient to provide the desired physical attributes and physical integrity to the composition, and binders also often function as thickening or gelling agents. Typical binders can be organic or inorganic, or a combination thereof. Representative binders include cellulose derivatives (e.g., cellulose ethers), povidone, sodium alginate, starch-based binders, pectin, gums, carrageenan, pullulan, zein, and the like, and combinations thereof. In some embodiments, the binder comprises pectin or carrageenan or combinations thereof.

The amount of binder utilized in the composition can vary based on the binder and the desired composition properties, but is typically up to about 30% by weight, and certain embodiments are characterized by a binder content of at least about 0.1% by weight, such as about 0.5 to about 30% by weight, or about 1 to about 10% by weight, based on the total weight of the composition.

In certain embodiments, the binder includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the composition.

In some embodiments, the binder comprises pectin. Pectins are natural polymers related to carbohydrates and which are acidic heteropolysaccharides (polysaccharides comprising multiple monosaccharide units). As opposed to carbohydrates, the pectin C-6 position contains a carboxylic acid (or corresponding methyl ester or carboxamide) group instead of a hydroxymethyl group. The principal subunit is known as galacturonic acid, which can be copolymerized with L-rhamnose. Other sugars are featured as side-chain substituents. Pectin acts as a thickening and gelling agent. Pectin isolated from sources such as apple pomace, citrus peels, sugarbeet waste from sugar manufacturing, sunflower heads discarded from seed harvesting, mango waste, and other commercially available pectins may be used. In combination with certain sugars, under acidic conditions (e.g., a pH of from about 2.5 to about 5), or in the presence of a gelation agent (calcium or other divalent alkaline earth elements), pectins may provide a gel or gum consistency to compositions as disclosed herein. In some embodiments, the binder comprises low methoxy pectin. Suitable low methoxy pectins include, for example, "GENU® pectin type LM-104 AS", available from CP Kelco, Atlanta, GA, USA. In some embodiments, the binder comprises low methoxy pectin in combination with a gelation agent. In some embodiments, the gelation agent comprises calcium ions, such as, but not limited to, calcium diphosphate. In some embodiments, the binder comprises a high methoxy pectin in combination with an organic acid, described herein below. In some embodiments, the binder comprises a high methoxy pectin in combination with citric acid.

When present, a pectin binder is typically present in an amount of up to about 3% by weight, for example, from about 0.1, about 0.2, about 0.3, about 0.4, about 0.5, about 0.6, about 0.7, about 0.8, about 0.9, or about 1, to about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, or about 3% by weight, based on the total weight of the composition.

Organic Acid

In some embodiments, the composition comprises an organic acid. As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($—CO_2H$) or sulfonic acids ($—SO_2OH$). As used herein, reference to organic acid means an organic acid that is intentionally added. In this regard, an organic acid may be intentionally added as a specific mixture ingredient as opposed to merely being inherently present as a component of another mixture ingredient (e.g., the small amount of organic acid which may inherently be present in a mixture ingredient such as a tobacco material). In some embodiments, the one or more organic acids are added neat (i.e., in their free acid, native solid or liquid form) or as a solution in, e.g., water. In some embodiments, the one or more organic acids are added in the form of a salt, as described herein below.

Suitable organic acids will typically have a range of lipophilicities (i.e., a polarity giving an appropriate balance of water and organic solubility). Lipophilicity is conveniently measured in terms of log P, the partition coefficient of a molecule between an aqueous and lipophilic phase, usually water and octanol, respectively. Typically, lipophilicities of organic acids may be between about −2 and about 6.5. In some embodiments, the organic acid may be more soluble in water than in octanol (i.e., having a negative log P value, such as from about −2 to about −1). In some embodiments, the organic acid may be about equally soluble in octanol than in water (i.e., having a log P value of about 0). In some embodiments, the organic acid may be more soluble in octanol than in water (i.e., having a positive log P value, such as from about 1 to about 6.5). In some embodiments, the organic acid has a log P value of from about 1.5 to about 5.0, e.g., from about 1.5, about 2.0, about 2.5, or about 3.0, to about 3.5, about 4.0, about 4.5, or about 5.0.

In some embodiments, the organic acid is a carboxylic acid or a sulfonic acid. The carboxylic acid or sulfonic acid functional group may be attached to any alkyl, cycloalkyl, heterocycloalkyl, aryl, or heteroaryl group having, for example, from one to twenty carbon atoms ($C_1$-$C_{20}$). In some embodiments, the organic acid is an alkyl, cycloalkyl, heterocycloalkyl, aryl, or heteroaryl carboxylic or sulfonic acid.

As used herein, "alkyl" refers to any straight chain or branched chain hydrocarbon. The alkyl group may be saturated (i.e., having all sp a carbon atoms), or may be unsaturated (i.e., having at least one site of unsaturation). As used herein, the term "unsaturated" refers to the presence of a carbon-carbon, sp 2 double bond in one or more positions within the alkyl group. Unsaturated alkyl groups may be mono- or polyunsaturated. Representative straight chain alkyl groups include, but are not limited to, methyl, ethyl, n-propyl, n-butyl, n-pentyl, and n-hexyl. Branched chain alkyl groups include, but are not limited to, isopropyl, sec-butyl, isobutyl, tert-butyl, isopentyl, and 2-methylbutyl. Representative unsaturated alkyl groups include, but are not limited to, ethylene or vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. An alkyl group can be unsubstituted or substituted.

"Cycloalkyl" as used herein refers to a carbocyclic group, which may be mono- or bicyclic. Cycloalkyl groups include rings having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted, and may include one or more sites of unsaturation (e.g., cyclopentenyl or cyclohexenyl).

The term "aryl" as used herein refers to a carbocyclic aromatic group. Examples of aryl groups include, but are not limited to, phenyl and naphthyl. An aryl group can be unsubstituted or substituted.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl group comprises up to 20 carbon atoms and from 1 to 3 heteroatoms selected from N, O, and S. A heteroaryl or heterocycloalkyl may be a monocycle having 3 to 7 ring members (for example, 2 to 6 carbon atoms and 1 to 3 heteroatoms selected from N, O, and S) or a bicycle having 7 to 10 ring members (for example, 4 to 9 carbon atoms and 1 to 3 heteroatoms selected from N, O, and S), for example: a bicyclo[4,5], [5,5], [5,6], or [6,6] system. Examples of heteroaryl groups include by way of example and not limitation, pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl. Examples of heterocycloalkyls include by way of example and not limitation, dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl. Heteroaryl and heterocycloalkyl groups can be unsubstituted or substituted.

"Substituted" as used herein and as applied to any of the above alkyl, aryl, cycloalkyl, heteroaryl, heterocyclyl, means that one or more hydrogen atoms are each independently replaced with a substituent. Typical substituents include, but are not limited to, —Cl, Br, F, alkyl, —OH, —OCH$_3$, NH$_2$, —NHCH$_3$, —N(CH$_3$)$_2$, —CN, —NC(=O)CH$_3$, —C(=O)—, —C(=O)NH$_2$, and —C(=O)N(CH$_3$)$_2$. Wherever a group is described as "optionally substituted," that group can be substituted with one or more of the above substituents, independently selected for each occasion. In some embodiments, the substituent may be one or more methyl groups or one or more hydroxyl groups.

In some embodiments, the organic acid is an alkyl carboxylic acid. Non-limiting examples of alkyl carboxylic acids include formic acid, acetic acid, propionic acid, octanoic acid, nonanoic acid, decanoic acid, undecanoic acid, dodecanoic acid, stearic acid, oleic acid, linoleic acid, linolenic acid, and the like. In some embodiments, the organic acid is an alkyl sulfonic acid. Non-limiting examples of alkyl sulfonic acids include propanesulfonic acid and octanesulfonic acid.

In some embodiments, the alkyl carboxylic or sulfonic acid is substituted with one or more hydroxyl groups. Non-limiting examples include glycolic acid, 4-hydroxybutyric acid, and lactic acid.

In some embodiments, an organic acid may include more than one carboxylic acid group or more than one sulfonic acid group (e.g., two, three, or more carboxylic acid groups). Non-limiting examples include oxalic acid, fumaric acid, maleic acid, and glutaric acid. In organic acids containing multiple carboxylic acids (e.g., from two to four carboxylic acid groups), one or more of the carboxylic acid groups may be esterified. Non-limiting examples include succinic acid monoethyl ester, monomethyl fumarate, monomethyl or dimethyl citrate, and the like.

In some embodiments, the organic acid may include more than one carboxylic acid group and one or more hydroxyl groups. Non-limiting examples of such acids include tartaric acid, citric acid, and the like. In some embodiments, the organic acid is citric acid, sodium citrate, calcium citrate, or a combination thereof.

In some embodiments, the organic acid is an aryl carboxylic acid or an aryl sulfonic acid. Non-limiting examples of aryl carboxylic and sulfonic acids include benzoic acid, toluic acids, salicylic acid, benzenesulfonic acid, and p-toluenesulfonic acid.

Additional non-limiting examples of suitable organic acids include 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), camphoric acid (+), camphor-10-sulfonic acid (+), capric acid, caproic acid, caprylic acid, cinnamic acid, cyclamic acid, decanoic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glycerophosphoric acid, glycolic acid, hippuric acid, isobutyric acid, lactobionic acid, lauric acid, malonic acid, mandelic acid, methanesulfonic acid, naphthalene-1,5-disulfonic acid, naphthalene-2-sulfonic acid, oleic acid, palmitic acid, pamoic acid, pyroglutamic acid, sebacic acid, stearic acid, and undecylenic acid.

In some embodiments, the one or more organic acids is a single organic acid. In some embodiments, the one or more organic acids is a combination of several acids, such as two, three, or more organic acids.

The amount of organic acid present in the composition may vary. Generally, the mixture comprises from about 0.1 to about 10% by weight of organic acid, present as one or more organic acids, based on the total weight of the composition. In some embodiments, the composition comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% organic acid by weight, based on the total weight of the composition. In some embodiments, the composition comprises from about 0.1 to about 0.5% by weight of organic acid, for example, about 0.1, about 0.15, about 0.2, about 0.25, about 0.3, about 0.35, about 0.4, about 0.45, or about 0.5% by weight, based on the total weight of the composition. In some embodiments, the composition comprises from about 0.25 to about 0.35% by weight of organic acid, for example, from about 0.25, about 0.26, about 0.27, about 0.28, about 0.29, or about 0.3, to about 0.31, about 0.32, about 0.33, about 0.34, or about 0.35% by weight, based on the total weight of the composition. In the case where a salt of an organic acid is added (e.g., sodium citrate), the percent by weight is calculated based on the weight of the free acid, not including any counter-ion which may be present.

Organic acids (e.g., citric acid) may be added neat (i.e., as a solid) or in solution, for example, in water. In some embodiments, the organic acid is added as a 50% aqueous solution.

Buffering Agents

In certain embodiments, the composition of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Non-limiting examples of suitable buffers include alkali metals acetates, glycinates, phosphates, glycerophosphates, citrates, carbonates, hydrogen carbonates, borates, or mixtures thereof. In some embodiments, the buffer is sodium bicarbonate.

Where present, the buffering agent is typically present in an amount less than about 5% by weight, based on the weight of the composition, for example, from about 0.1% to about 5%, such as, e.g., from about 0.1% to about 1%, or from about 0.1% to about 0.5% by weight, based on the total weight of the composition.

Colorants

A colorant may be employed in amounts sufficient to provide the desired physical attributes to the composition. Examples of colorants include various dyes and pigments, such as caramel coloring and titanium dioxide. Natural colorants such as curcumin, beet juice extract, spirulina; also a variety of synthetic pigments may also be used. The amount of colorant utilized in the composition can vary, but when present is typically up to about 3% by weight, such as from about 0.1%, about 0.5%, or about 1%, to about 3% by weight, based on the total weight of the composition.

Humectants

In certain embodiments, one or more humectants may be employed in the composition. Examples of humectants include, but are not limited to, glycerin, propylene glycol, and the like. Where included, the humectant is typically provided in an amount sufficient to provide desired moisture attributes to the composition. Further, in some instances, the humectant may impart desirable flow characteristics to the composition for depositing in a mold. When present, a humectant will typically make up about 5% or less of the weight of the composition (e.g., from about 0.1 to about 5% by weight), for example, from about 0.1% to about 1% by weight, or about 1% to about 5% by weight, based on the total weight of the composition.

Oral Care Additives

In some embodiments, the composition comprises an oral care ingredient (or mixture of such ingredients). Oral care ingredients provide the ability to inhibit tooth decay or loss, inhibit gum disease, relieve mouth pain, whiten teeth, or otherwise inhibit tooth staining, elicit salivary stimulation, inhibit breath malodor, freshen breath, or the like. For example, effective amounts of ingredients such as thyme oil, eucalyptus oil and zinc (e.g., such as the ingredients of formulations commercially available as ZYTEX® from Discus Dental) can be incorporated into the composition. Other examples of ingredients that can be incorporated in desired effective amounts within the present composition can include those that are incorporated within the types of oral care compositions set forth in Takahashi et al., Oral Microbiology and Immunology, 19(1), 61-64 (2004); U.S. Pat. No. 6,083,527 to Thistle; and US Pat. Appl. Pub. Nos. 2006/0210488 to Jakubowski and 2006/02228308 to Cummins et al. Other exemplary ingredients of tobacco containing—formulation include those contained in formulations marketed as MALTISORB® by Roquette and DENTIZYME® by NatraRx. When present, a representative amount of oral care additive is at least about 1%, often at least about 3%, and frequently at least about 5% of the total dry weight of the composition. The amount of oral care additive within the composition will not typically exceed about 30%, often will not exceed about 25%, and frequently will not exceed about 20%, of the total dry weight of the composition.

Processing Aids

If necessary for downstream processing of the composition, such as granulation, mixing, or molding, a flow aid can also be added to the composition in order to enhance flowability of the composition. In some embodiments, the composition (e.g., melt and chew forms) may be surface treated with anti-stick agents, such as oils, silicones, and the like. Exemplary flow aids include microcrystalline cellulose, silica, polyethylene glycol, stearic acid, calcium stearate, magnesium stearate, zinc stearate, sodium stearyl fumarate, canauba wax, and combinations thereof. In some embodiments, the flow aid is sodium stearyl fumarate.

When present, a representative amount of flow aid may make up at least about 0.5 percent or at least about 1 percent, of the total dry weight of the composition. Preferably, the amount of flow aid within the composition will not exceed about 5 percent, and frequently will not exceed about 3 percent, of the total dry weight of the composition.

Emulsifier

In certain embodiments, an emulsifier may be added. In some embodiments, the emulsifier is lecithin. For example, lecithin (e.g., soy lecithin or sunflower lecithin) may be added to the composition to provide smoother textural properties to the composition and to improve flowability and mixing of e.g., a lipid with the remaining components of the composition. Emulsifiers (e.g., lecithin) can be used in an amount of about 0.01 to about 5% by dry weight of the composition, such as from about 0.1 to about 2.5%, or from about 0.5 to about 1.5% based on the total weight of the composition.

Other Additives

Other additives can be included in the disclosed composition. For example, the composition can be processed, blended, formulated, combined, and/or mixed with other materials or ingredients. The additives can be artificial, or can be obtained or derived from herbal or biological sources. Examples of further types of additives include thickening or gelling agents (e.g., fish gelatin), emulsifiers, preservatives (e.g., potassium sorbate and the like), disintegration aids, zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final composition, with an example range of up to about 10% by weight, based on total weight of the composition (e.g., about 0.1 to about 5% by weight).

The aforementioned additives can be employed together (e.g., as additive formulations) or separately (e.g., individual additive components can be added at different stages involved in the preparation of the final composition). Furthermore, the aforementioned types of additives may be encapsulated as provided in the final product or composition. Exemplary encapsulated additives are described, for example, in WO2010/132444 to Atchley, which has been previously incorporated by reference herein.

Configured for Oral Use

Provided herein is a composition configured for oral use. The term "configured for oral use" as used herein means that the composition is provided in a form such that during use, saliva in the mouth of the user causes one or more of the components of the composition (e.g., flavoring agents and/or cannabinoids) to pass into the mouth of the user. In certain embodiments, the composition is adapted to deliver components to a user through mucous membranes in the user's mouth, the user's digestive system, or both, and, in some instances, said component is a cannabinoid or cannabimimetic (including, but not limited to, for example, tetrahydrocannabinol (THC), cannabidiol (CBD), and combinations thereof) that can be absorbed through the mucous membranes in the mouth or absorbed through the digestive tract when the product is used.

The compositions as disclosed herein can be formed into a variety of shapes, including pills, tablets, spheres, strips, films, sheets, coins, cubes, beads, ovoids, obloids, cylinders, bean-shaped, sticks, or rods. Cross-sectional shapes of the composition can vary, and example cross-sectional shapes include circles, squares, ovals, rectangles, and the like. Such shapes can be formed in a variety of manners using equipment such as moving belts, nips, extruders, granulation devices, compaction devices, and the like.

The composition can be meltable as discussed, for example, in US Patent App. Pub. No. 2012/0037175 to Cantrell et al., incorporated by reference herein in its entirety. As used herein, "melt," "melting," and "meltable" refer to the ability of the composition to change from a solid state to a liquid state. That is, melting occurs when a substance (e.g., a composition as disclosed herein) changes from solid to liquid, usually by the application of heat. The application of heat in regard to a composition as disclosed herein is provided by the internal temperature of a user's mouth. Thus, the term "meltable" refers to a composition that is capable of liquefying in the mouth of the user as the composition changes phase from solid to liquid, and is intended to distinguish compositions that merely disintegrate in the oral cavity through loss of cohesiveness within the composition that merely dissolve in the oral cavity as aqueous-soluble components of the composition interact with moisture. Generally, meltable compositions comprise a lipid as described herein above. In some embodiments, the composition in meltable form comprises a lipid in an amount of from about 35 to about 58% by weight, based on the total weight of the composition, and a sugar alcohol in an amount of from about 38 to about 58% by weight, based on the total weight of the composition. In some embodiments, the sugar alcohol is isomalt, erythritol, sorbitol, arabitol, ribitol, maltitol, dulcitol, iditol, mannitol, xylitol, lactitol, or a combination thereof. In some embodiments, the sugar alcohol is isomalt.

Preparation of the Composition

The manner by which the various components of the composition (e.g., filler, cannabinoid, and the like) are combined may vary. As such, the overall composition with e.g., powdered composition components may be relatively uniform in nature (e.g., homogenous). The components noted above, which may be in liquid or dry solid form, can be admixed in a pretreatment step prior to mixture with any remaining components of the composition, or simply mixed together with all other liquid or dry ingredients. The compositions of the disclosure are prepared, for example, by dry-blending dry ingredients, such as filler, sweeteners, salts, and the like. In certain embodiments, water can be added to the dry blend at this stage. Additionally, it is optional to add, such as by spraying, cannabinoids and/or flavoring agents to the dry blend, followed by mixing.

The various components of the composition may be contacted, combined, or mixed together using any mixing technique or equipment known in the art. Any mixing method that brings the composition ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Ploughshare® types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components forming the composition are prepared such that the mixture thereof may be used in a starch molding process for forming the composition. Manners and methods for formulating compositions will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

For preparation of meltable compositions, the lipid is typically heated to slightly above the melting temperature such that the lipid is liquefied. Optionally, cannabinoids, flavoring agents, and/or lecithin can be added to the liquefied lipid at this stage. Thereafter, all or a portion of the liquefied lipid can be blended with the dry blend and mixed until the composition reaches the desired level of homogeneity or until the desired textural properties are achieved. The mixture can be milled (e.g., in a dry roll mill) until the particle size is less than about 20 microns. The milled isomalt-palm oil mixture can be combined with any remaining lipid, and the dry ingredients and flavor mixed in. The base is generally warmed to a fluid consistency. The composition can be divided into discrete portions, such as by pouring the composition into a sheet-like structure, cooling, and then cutting the structure into individual portions, or by depositing the composition into molds and allowing to cool.

In one embodiment, for example, a lipid (e.g., including a combination of palm oil and palm kernel oil) may be heated to slightly above the melting temperature to form a melted material (e.g., such that the lipid is in liquefied form). Thereafter, a portion of the melted lipid material may be admixed with a filler material (e.g., such as isomalt), using one or more mixing techniques or apparatuses as described herein above, to form a mixture. Optionally, one or more additional ingredients (e.g., such as flavors, salts, sweeteners, and/or lecithin) may be admixed with the melted lipid material and the filler material during this step. Generally during mixing of the lipid and filler material clumps may begin to form in the mixture and the mixture may optionally be milled to form a powder having a desired particle size. For example, in some embodiments, the mixture can be milled (e.g., in a dry roll mill) until the particle size is less than about 20 microns. Thereafter, the remainder of the melted lipid material may be admixed with the milled powder to form a base material and the base material is warmed to a fluid consistency. The base material may then be admixed with at least one cannabinoid (e.g., CBD) or cannabimimetic and optionally other ingredients (e.g., such as sweeteners, salts, flavorants, buffers, emulsifiers, colorants, processing aids, and the like) to form a meltable composition. Optionally, in some embodiments, the at least one cannabinoid or cannabimimetic may be premixed with a separate lipid oil (e.g., such as sunflower oil) to form a premixed solution prior to combination with the base material. In such embodiments, for example, the premixed solution may include a mixture of the at least one cannabinoid or cannabimimetic and a lipid oil that remains a liquid at room temperature, e.g., such as sunflower oil. Thereafter, the premixed solution and optionally other ingredients (e.g., such as sweeteners, salts, flavorants, buffers, emulsifiers, colorants, processing aids, and the like) can be admixed with the heated base material to form a meltable composition.

The meltable composition can be divided into discrete portions, such as by pouring the composition into a sheet-like structure, cooling, and then cutting the structure into individual portions, or by depositing the composition into molds (e.g., via a heated depositing funnel) and allowing to meltable composition within the individual molds to cool and solidify, prior to removal from the molds.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Example

Aspects of the present invention are more fully illustrated by the following example, which is set forth to illustrate certain aspects of the present invention and is not to be construed as limiting thereof.

A composition according to an embodiment of the present disclosure in meltable form was prepared from a composition containing a filler, a lipid, a cannabinoid (e.g., CBD), and additional components as disclosed herein (salt, sweeteners, flavoring agent). The ingredients of the composition and their concentrations in the final product in weight % are provided in Table 1.

TABLE 1

Meltable ingredients

| Ingredient | % w/w |
| --- | --- |
| Isomalt | 38-58 |
| Lipid (e.g., mixture of palm kernel oil and palm oil) | 35-53 |
| Cannabinoid | 0.1-5 |
| Salt | 0.5-1.5 |
| Sunflower lecithin | 0.5-1.5 |
| Sunflower oil | 2-6 |
| Sweetener | 0.05-0.5 |
| flavor | 0.5-1.5 |

The meltable product was formed using the following general procedure. A portion of the palm oil/palm kernel oil (lipid) was melted and mixed with the isomalt in a mixer until clumps begin to form. The mixture was transferred to a dry roll mill and milled until the particle size was less than 20 microns. In a mixer, the milled isomalt-palm oil material was combined with the remaining portion of palm oil, salt (e.g., NaCl), and sunflower lecithin to form a base mixture.

The base mixture was warmed to a fluid consistency. A premixed solution of sunflower oil and cannabinoid was formed. The premixed solution, sweetener, and flavor were mixed in with the warmed base. The isomalt-palm oil-ingredient mixture was transferred to a heated depositing funnel. The appropriate weight of the samples was deposited into a shape mold. If needed, the mold was placed on a vibrator to ensure even filling. The product was allowed to cool and solidify, then removed from the mold. The melts each weighed 1500 mg.

What is claimed is:

1. A meltable composition configured for oral use, the composition comprising:
   a cannabinoid or cannabimimetic;
   a filler comprising at least one sugar alcohol;
   a first lipid comprising palm oil, partially hydrogenated palm oil, hydrogenated palm oil, palm kernel oil, partially hydrogenated palm kernel oil, hydrogenated palm kernel oil, soybean oil, partially hydrogenated soybean oil, hydrogenated soybean oil, sunflower oil, partially hydrogenated sunflower oil, hydrogenated sunflower oil, cottonseed oil partially hydrogenated cottonseed oil, hydrogenated cottonseed oil, coconut oil, partially hydrogenated coconut oil, hydrogenated coconut oil, or a combination thereof;
   a second lipid having a melting point of about 25° C. or lower; and
   water in an amount by weight from about 0.1 to about 1%, based on the total weight of the composition;
   wherein a total amount of the first and second lipid is from about 35 to about 58% by weight, based on the total weight of the composition.

2. The meltable composition of claim 1, wherein the first lipid comprises palm oil, palm kernel oil, soybean oil, sunflower oil, cottonseed oil, coconut oil, or a combination thereof.

3. The meltable composition of claim 1, wherein the first lipid comprises palm oil, palm kernel oil, or a mixture thereof.

4. The meltable composition of claim 1, wherein the second lipid is selected from the group consisting of acai oil, almond oil, amaranth oil, apricot oil, apple seed oil, argan oil, avocado oil, babassu oil, beech nut oil, ben oil, bitter gourd oil, black seed oil, blackcurrant seed oil, borage seed oil, borneo tallow nut oil, bottle gourd oil, brazil nut oil, buffalo gourd oil, butternut squash seed oil, cape chestnut oil, canola oil, carob cashew oil, cocklebur oil, coconut oil, corn oil, cothune oil, coriander seed oil, cottonseed oil, date seed oil, dika oil, egus seed oil, evening primrose oil, false flax oil, flaxseed oil, grape seed oil, grapefruit seed oil, hazelnut oil, hemp oil, kapok seed oil, kenaf seed oil, lallemantia oil, lemon oil, linseed oil, macadamia oil, mafura oil, manila oil, meadowfoam seed oil, mongongo nut oil, mustard oil, niger seed oil, okra seed oil, olive oil, orange oil, papaya seed oil, peanut oil, pecan oil, perilla seed oil, persimmon seed oil, pequi oil, pili nut oil, pine nut oil, pistachio oil, pomegranate seed oil, poppyseed oil, pracaxi oil, prune kernel oil, pumpkin seed oil, quinoa oil, ramtil oil, rapeseed oil, rice bran oil, royle oil, sacha inchi oil, safflower oil, sapote oil, seje oil, sesame oil, soybean oil, sunflower oil, taramira oil, tea seed oil, thistle oil, tigernut oil, tobacco seed oil, tomato seed oil, walnut oil, watermelon seed oil, wheat germ oil, and combinations thereof.

5. The meltable composition of claim 1, wherein the second lipid is present in an amount of from about 2 to about 6% by weight, based on the total weight of the composition.

6. The meltable composition of claim 1, comprising from about 38 to about 58% by weight of the at least one sugar alcohol, based on the total weight of the composition.

7. The meltable composition of claim 1, wherein the at least one sugar alcohol comprises isomalt, maltitol, a glucose-polysaccharide blend, erythritol, sorbitol, arabitol, ribitol, dulcitol, iditol, mannitol, xylitol, lactitol, or a combination thereof.

8. The meltable composition of claim 1, wherein the at least one sugar alcohol comprises isomalt, maltitol, a glucose-polysaccharide blend, or a combination thereof.

9. The meltable composition of claim 1, further comprising lecithin in an amount of from about 0.5 to about 1.5% by weight, based on the total weight of the composition.

10. The meltable composition of claim 1, wherein the cannabinoid or cannabimimetic is present in an amount of from about 0.1 to about 20% by weight, based on the total weight of the composition.

11. The meltable composition of claim 1, wherein the cannabinoid is selected from the group consisting of cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), tetrahydrocannabivarinic acid (THCV A), and combinations thereof.

12. The meltable composition of claim 1, wherein the cannabinoid is selected from the group consisting of tetrahydrocannabinol (THC), cannabidiol (CBD), and combinations thereof.

13. The meltable composition of claim 1, wherein the composition further comprises an additional active ingredient selected from the group consisting of botanical ingredients, stimulants, amino acids, nicotine components, pharmaceutical ingredients, nutraceutical ingredients, medicinal ingredients, terpenes, and combinations thereof.

14. The meltable composition of claim 13, wherein the composition comprises a terpene selected from the group consisting of beta-caryophyllene, linalool, limonene, beta-citronellol, linalyl acetate, alpha pinene, beta pinene, geraniol, carvone, eucalyptol, menthone, iso-menthone, piperitone, myrcene, beta-bourbonene, germacrene, and combinations thereof.

15. The meltable composition of claim 1, further comprising at least one additional component selected from sweeteners, salts, flavorants, buffers, emulsifiers, colorants, processing aids, and combinations thereof.

16. The meltable composition of claim 1, wherein the composition is substantially free of nicotine.

* * * * *